(12) United States Patent
Ushijima et al.

(10) Patent No.: US 8,469,878 B2
(45) Date of Patent: Jun. 25, 2013

(54) HOOD ATTACHMENT JIG

(75) Inventors: Takanori Ushijima, Tama (JP); Katsuya Kono, Morioka (JP)

(73) Assignee: Olympus Medical Systems Corp., Tokyo (JP)

( * ) Notice: Subject to any disclaimer, the term of this patent is extended or adjusted under 35 U.S.C. 154(b) by 438 days.

(21) Appl. No.: 12/791,073

(22) Filed: Jun. 1, 2010

(65) Prior Publication Data

US 2010/0305404 A1    Dec. 2, 2010

Related U.S. Application Data

(63) Continuation of application No. PCT/JP2009/068691, filed on Oct. 30, 2009.

(30) Foreign Application Priority Data

Dec. 17, 2008 (JP) ................. 2008-321287
Dec. 17, 2008 (JP) ................. 2008-321288

(51) Int. Cl.
*A61B 1/00* (2006.01)
*A61B 1/04* (2006.01)

(52) U.S. Cl.
USPC ............................. 600/101; 600/124; 600/127

(58) Field of Classification Search
USPC .................. 600/101, 104, 121–125, 127–129
See application file for complete search history.

(56) References Cited

U.S. PATENT DOCUMENTS 6,049,960 A * 4/2000 Pilling et al. ............... 29/450
7,591,782 B2 * 9/2009 Fujikura ..................... 600/116
2002/0091303 A1 7/2002 Ootawara et al.
2004/0077926 A1 4/2004 Moriyama
2011/0105840 A1 * 5/2011 Terliuc et al. ............... 600/104

FOREIGN PATENT DOCUMENTS

| JP | 2605549 Y2 | 5/2000 |
| JP | 2002-545 A | 1/2002 |
| JP | 2003-230531 A | 8/2003 |
| JP | 2004-229987 A | 8/2004 |
| JP | 2004-298442 A | 10/2004 |
| JP | 2006-314804 A | 11/2006 |

OTHER PUBLICATIONS

International Search Report dated Dec. 22, 2009.

* cited by examiner

*Primary Examiner* — Alireza Nia
(74) *Attorney, Agent, or Firm* — Scully, Scott, Murphy & Presser, P.C.

(57) ABSTRACT

A hood attachment jig includes a holding member whose diameter is increasable and that holds an endoscope hood in a state where the holding member is inserted into the endoscope hood; a diameter increasing member that increases the diameter of the holding member by entering the holding member, so that the diameter of the endoscope hood increases; and a push-out member that, when an attachment operation is performed in a state where a tip portion of the endoscope enters the holding member with the increased diameter, pushes out the holding member and the endoscope to separate the holding member and the endoscope from the diameter increasing member so that the endoscope hood, a force of restitution of which reduces the diameter of the holding member, is brought into contact with an outer circumferential surface of the tip portion of the endoscope and further pushes out the endoscope to detach the endoscope from the holding member so that the endoscope hood is attached to the endoscope tip portion.

9 Claims, 14 Drawing Sheets

HOOD ATTACHMENT JIG

CROSS-REFERENCE TO RELATED APPLICATIONS

This application is a continuation of PCT international application Ser. No. PCT/JP2009/068691 filed Oct. 30, 2009 which designates the United States, incorporated herein by reference, and which claims the benefit of priority from Japanese Patent Applications No. 2008-321287, and No. 2008-321288, both filed Dec. 17, 2008, all incorporated herein by reference.

BACKGROUND OF THE INVENTION

1. Field of the Invention

The present invention relates to a hood attachment jig. More specifically, the present invention relates to a hood attachment jig for attaching an approximately cylindrical endoscope hood to an endoscope such that the endoscope hood covers the outer circumferential surface of a tip portion of the endoscope.

2. Description of the Related Art

Conventionally, the jigs described in the following are known as hood attachment jigs for attaching an approximately cylindrical endoscope hood to an endoscope such that the endoscope hood covers the external circumferential surface of a tip portion of the endoscope. For example, there is a hood attachment jig that is connected to the base end peripheral portion of the endoscope hood via a connecting member and that includes a grip that extends outward from the outer circumferential surface of the base end peripheral portion. In other words, the hood attachment jig is configured integrally with the endoscope hood.

When the grip of such a hood attachment jig is grasped between the fingers, the base end peripheral portion of the endoscope hood is move outward so that the diameter of the base end portion of the endoscope hood increases. The endoscope tip portion relatively enters the base end portion with the increased diameter. Thereafter, the grip is released so that the diameter of the base end portion decreases. Accordingly, the endoscope hood can be attached to the endoscope tip portion. After the endoscope hood is attached to the endoscope tip portion, a previously formed fragile portion is fractured so that the hood attachment jig is detached from the endoscope hood.

SUMMARY OF THE INVENTION

A hood attachment jig according to an aspect of the present invention is a hood attachment jig for attaching an approximately cylindrical endoscope hood to an endoscope such that the endoscope hood covers a circumferential surface of a tip portion of the endoscope. The hood attachment jig includes a holding member whose diameter is increasable and that holds the endoscope hood in a state where the holding member is inserted into the endoscope hood; a diameter increasing member that increases the diameter of the holding member by entering the holding member, so that the diameter of the endoscope hood increases; and a push-out member that, when an attachment operation is performed in a state where the tip portion of the endoscope enters the holding member with the increased diameter, pushes out the holding member and the endoscope to separate the holding member and the endoscope from the diameter increasing member so that the endoscope hood, a force of restitution of which reduces the diameter of the holding member, is brought into contact with an outer circumferential surface of the tip portion of the endoscope and further pushes out the endoscope to detach the endoscope from the holding member so that the endoscope hood is attached to the endoscope tip portion.

A hood attachment jig according to another aspect of the present invention is a hood attachment jig for attaching an approximately cylindrical endoscope hood to an endoscope such that the endoscope hood covers a circumferential surface of a tip portion of the endoscope. The hood attachment jig includes a holding means whose diameter is increasable and that holds the endoscope hood in a state where the holding means is inserted into the endoscope hood; a diameter increasing means for increasing the diameter of the holding means by entering the holding means, so that the diameter of the endoscope hood increases; and a push-out means for, when an attachment operation is performed in a state where the tip portion of the endoscope enters the holding means with the increased diameter, pushing out the holding means and the endoscope to separate the holding means and the endoscope from the diameter increasing means so that the endoscope hood, a force of restitution of which reduces the diameter of the holding means, is brought into contact with an outer circumferential surface of the tip portion of the endoscope and further pushing out the endoscope to detach the endoscope from the holding means so that the endoscope hood is attached to the endoscope tip portion.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Preferred embodiments of a hood attachment jig according to the present invention will be explained in detail below with reference to the accompanying drawings. First, an endoscope hood that is attached to an endoscope tip portion using the hood attachment jig according to the embodiment of the present invention will be explained.

Figure 1:
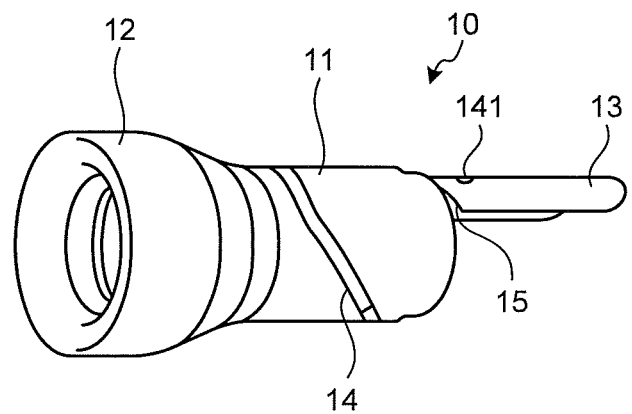
FIG. 1 is a perspective view of an endoscope hood that is attached to a tip portion of an endoscope using a hood attachment jig according to an embodiment of the present invention.
Figure 2:
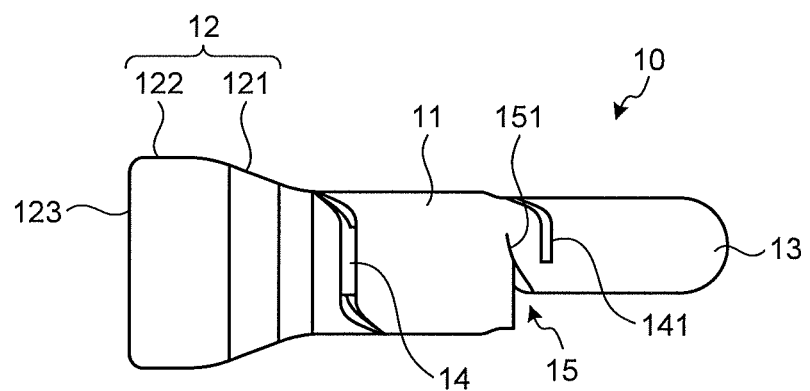
FIG. 2 is a view of the endoscope hood that is illustrated in FIG. 1 and viewed approximately from the side.
Figure 3:
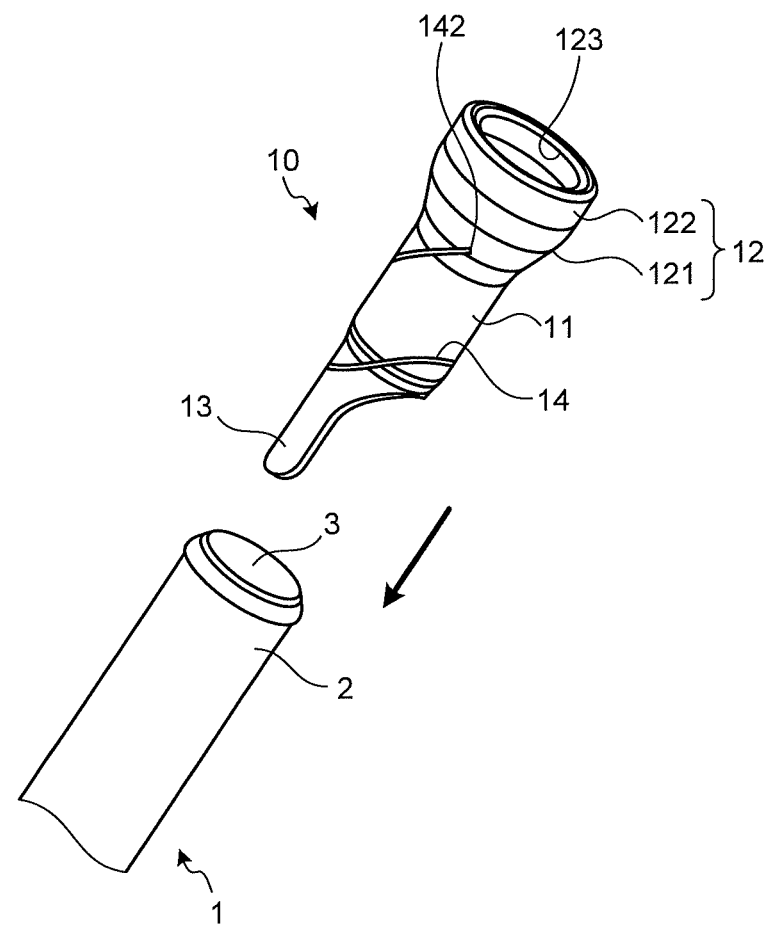
FIG. 3 is an explanatory view illustrating a case where the endoscope hood illustrated in FIG. 1 is about to be attached to the tip portion of the endoscope.
Figure 4:
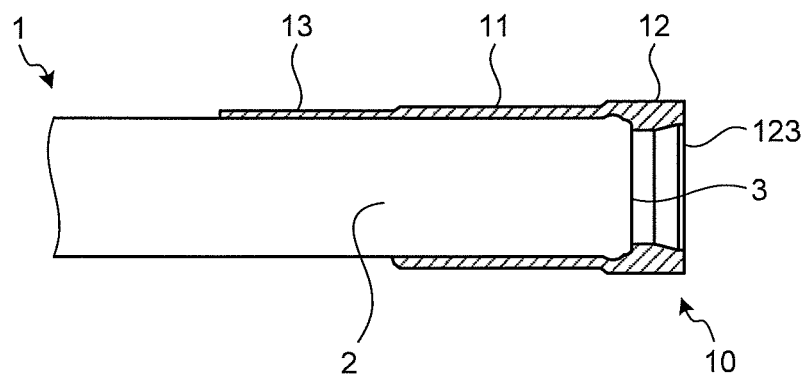
FIG. 4 is a cross-sectional side view illustrating a case where the endoscope hood illustrated in FIG. 1 is attached to the tip portion of the endoscope.

FIGS. 1 to 4 each illustrate the endoscope hood that is attached to the tip portion of the endoscope using the hood attachment jig according to the embodiment of the present invention. FIG. 1 is a perspective view of the hood attachment jig, FIG. 2 is an approximately side view of the endoscope hood that is illustrated in FIG. 1, FIG. 3 illustrates a case where the endoscope hood is about to be attached to the tip portion of the endoscope, and FIG. 4 is a cross-sectional side view illustrating a case where the endoscope hood is attached to the tip portion of the endoscope. An endoscope hood 10 illustrated below is attached to a tip portion 2 of an endoscope 1. The endoscope hood 10 is configured to include a fixation portion 11, a protruding portion 12, and a grip 13.

The fixation portion 11 is cylindrical. When the endoscope hood 10 is attached to the tip portion 2 of the endoscope 1, as illustrated in FIG. 4, the fixation portion 11 is fixed by pressure such that the fixation portion 11 covers the outer circumferential surface of the tip portion 2 of the endoscope 1.

The protrusion portion 12 is formed to be contiguous to the tip of the fixation portion 11 and has an approximately cylindrical shape. In the protrusion portion 12, a portion 121 has a tapered shape in which the diameter of the portion 121 that is close to the fixation portion 11 increases from the fixation portion, i.e., toward the tip of the protrusion portion 12, and a tip portion 122 is cylindrical.

The protrusion portion 12 is formed to have a thickness larger than that of the fixation portion 11. When the endoscope hood 10 is attached to the tip portion 2 of the endoscope 1 as illustrated in FIG. 4, the protrusion portion 12 protrudes beyond a tip 3 of the endoscope 1. This keeps the tip 3 of the endoscope 1 and a living organism separated from each other. In addition, an opening 123 is formed at the tip of the protrusion portion 12. Through the opening 123, a living tissue can be observed.

The grip 13 is formed to be contiguous to the base end of the fixation portion 11a and is tongue-shaped. The grip 13 is formed to have a thickness smaller than that of the fixation portion 11. When the endoscope hood 10 is attached to the tip portion 2 of the endoscope 1, as illustrated in FIG. 4, the grip 13 is positioned to be brought into contact with the outer circumferential surface of the endoscope 1.

The endoscope hood 10 is formed of, for example, a synthetic resin material and thus has elasticity. In the embodiment, the endoscope hood 10 is formed of a resin material that contains an added contrast agent such that observation can be performed using a contrast technique. Various types of conventional contrast agents may be used. In addition, the amount of the contrast agent added is not particularly limited as long as it does not reduce the elasticity of the resin material and it leads to the contrast effects.

In addition to the above configuration, a groove portion 14 and a cutout 15 are formed in the endoscope hood 10. The groove portion 14 is formed to be cut into and spirally on the outer surface of the fixation portion 11 such that an end 141 extends along the outer surface of the grip 13 and another end 142 extends along the outer surface of the protrusion portion 12. The groove portion 14 is formed to have a thickness smaller than those of the fixation portion 11, the protrusion portion 12, and the grip 13.

The cutout 15 is a boundary between the fixation portion 11 and the grip 13 and is formed on the base portion of the grip 13. The cutout 15 extends approximately in the circumferential direction of the fixation portion 11. An extension end portion 151 of the cutout 15 is positioned between the end 141 of the groove portion 14 and the groove portion 14 that is adjacent to the end 141. In other words, the cutout 15 extends between the end 141 of the groove portion 14 and the same groove portion 14 that is adjacent to the end 141.

The endoscope hood 10 that has the above-described configuration is attached to the tip portion 2 of the endoscope 1 as follows. Although it is not clearly illustrated in the drawings, the diameter of the endoscope hood 10 is increased using a dedicated jig. In other words, the diameter of the fixation portion 11 and the diameter of the protrusion portion 12 are increased and the tip portion 2 of the endoscope 1 relatively enters the endoscope hood 10 with the increased diameter (for example, see FIG. 3). Thereafter, the diameter of the endoscope hood 10 decreases because of the force of restitution of the material of the endoscope hood 10 so that the endoscope hood 10 is attached to the tip portion 2 of the endoscope 1 as illustrated in FIG. 4.

The groove portion 14 with the smallest thickness is formed spirally and has no portion that extends in the axial direction of the fixation portion 11. Thus, there is no risk that the endoscope hood 10 is torn when the diameter of the endoscope hood 10 increases (i.e., when the diameter of the fixation portion 11 and the diameter of the protrusion portion 12 increase).

The endoscope hood 10 that is attached to the tip portion of the endoscope 1 is detached from the endoscope 1 as follows. Although it is not clearly illustrated in the drawings, a user grasps the grip 13 and pulls the grip 13 to move up the grip 13 in the axial direction of the fixation portion 11 so that the endoscope hood 10 is torn from the cutout 15 (the extension end portion 151). Because the extension end portion 151 of the cutout 15 is positioned between the end 141 of the groove portion 14 and the same groove portion 14 adjacent to the end 141, the tearing from the cutout 15 reaches any one site on the groove portion 14. Thereafter, the endoscope hood 10 is torn in the direction in which the groove portion 14 extends so that the fixation portion 11 fractures.

Because the groove portion 14 is formed spirally, there is no risk that the endoscope hood 10 is torn when the diameter of the fixation portion 11 and the diameter of the protrusion portion 12 increase. Accordingly, the endoscope hood 10 can be easily attached to the endoscope 1. Particularly, in a hood that is to be attached to the endoscope 1 with a sufficiently small diameter, the thickness of the groove portion 14 is significantly small. However, because the groove portion 14 is formed spirally, there is no risk that the hood is torn when the diameter of the hood is increased. Accordingly, the hood can be easily attached to the endoscope 1 with a small diameter.

In addition, because the cutout 15 is positioned between the end 141 of the groove portion 14 and the same groove portion 14 adjacent to the end 141, the tearing from the cutout 15 reaches any one site on the groove portion 14. The hood is then torn in the direction in which the groove portion 14 extends and thus the fixation portion 11 fractures so that the endoscope hood 10 can be detached easily. The same applies to a case when the hood is attached to the endoscope 1 with a small diameter.

Accordingly, the endoscope hood 10 can be attached preferably to the endoscope 1 that has a sufficiently small diameter and also can be detached easily.

Furthermore, in the endoscope hood 10, the grip 13 is formed to have a thickness smaller than that of the fixation portion 11. This prevents the grip 13 from rolling back when the endoscope hood 10 is attached to the endoscope 1. Thus, when a living organism is observed, there is no risk that the grip 13 rolls back and thus the living tissue is damaged.

Furthermore, because the endoscope hood 10 is formed of a material that contains an added contrast agent, observation can be performed using the contrast technique.

Figure 5:
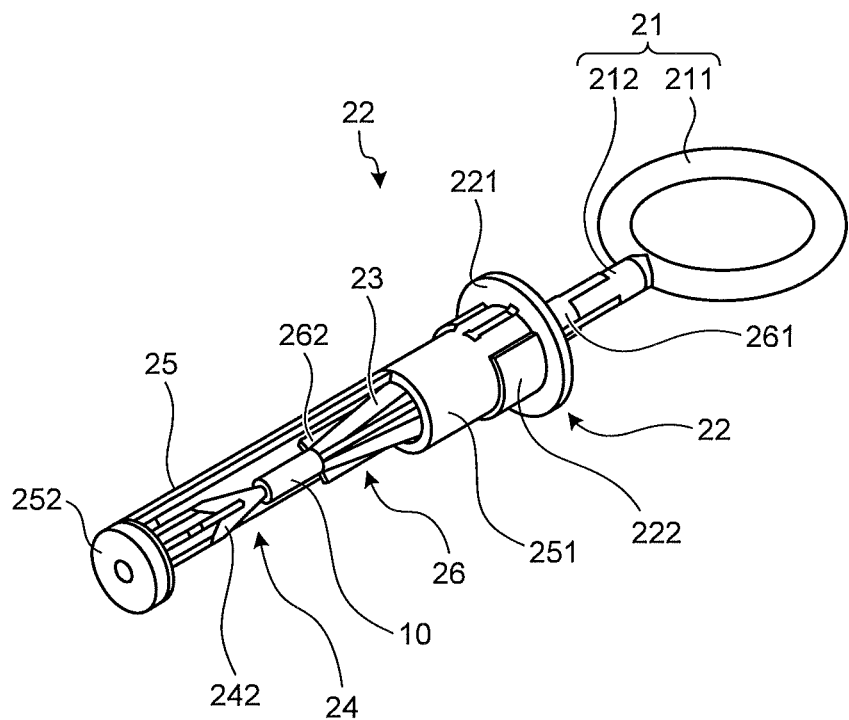
FIG. 5 is a perspective view of the hood attachment jig according to the embodiment of the present invention.
Figure 6A:
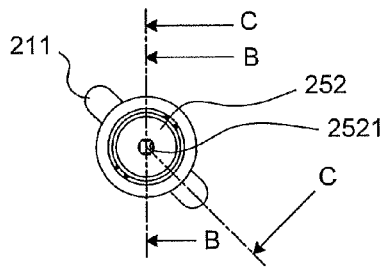
FIG. 6A is a front view of the hood attachment jig according to the embodiment of the present invention.
Figure 6B:
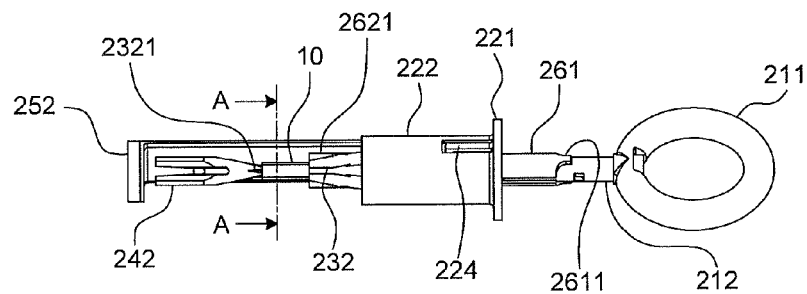
FIG. 6B is a side view of FIG. 6A.
Figure 6C:
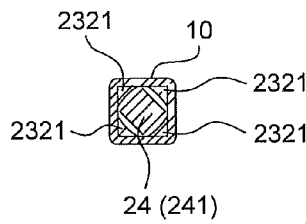
FIG. 6C is a cross-sectional view along the line A-A in FIG. 6B.
Figure 6D:
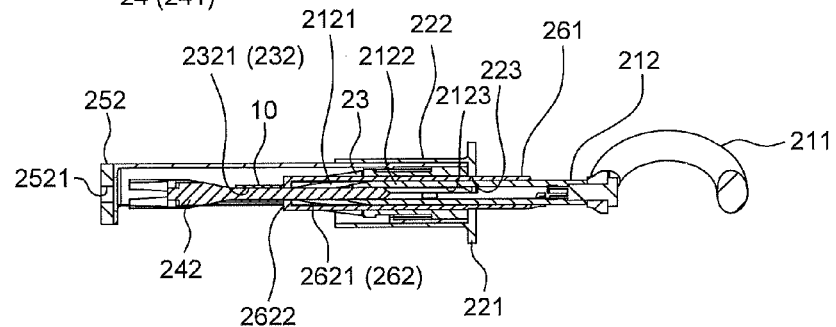
FIG. 6D is a cross-sectional view along the line B-B in FIG. 6A.
Figure 6E:
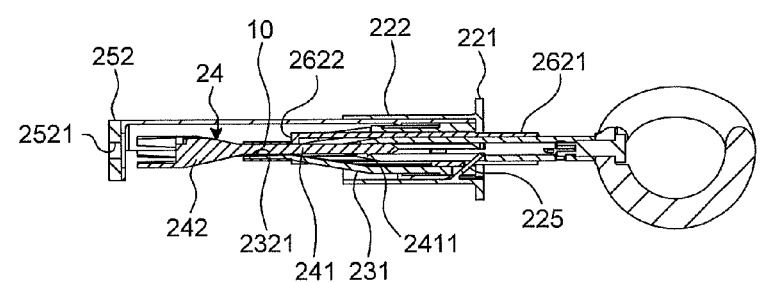
FIG. 6E is a cross-sectional view along the line C-C in FIG. 6A.

The hood attachment jig will be explained next. FIGS. 5 and 6 each illustrate the hood attachment jig according to the embodiment of the present invention. FIG. 5 is a perspective view of the hood attachment jig, FIG. 6A is a front view of the hood attachment jig, FIG. 6B is a side view of FIG. 6A, FIG. 6C is a cross-sectional view along the line A-A in FIG. 6B, FIG. 6D is a cross-sectional view along the line B-B in FIG. 6A, and FIG. 6E is a cross-sectional view along the line C-C in FIG. 6A. A hood attachment jig 20 illustrated here is formed of, for example, a synthetic resin. The hood attachment jig 20 is configured to include an operation member 21, a cover member 22, a holding member 23, a diameter increasing member 24, and an external cylindrical member 25. Hereinafter, in this specification, explanation will be provided assuming that the front side of the hood attachment jig 20 is the forward side and the back side of the hood attachment jig 20 is the backward side.

The operation member 21 includes an operation portion 211 and a hook portion 212. The operation portion 211 has a ring shape. The hook portion 212 has a rod shape and extends along the front side portion of the operation portion 211 in the radial outer direction of the operation portion 211, i.e., extends anteroposteriorly to the front side. The hook portion 212 is arranged to be rotatable about the center axis of the hook portion 212, which serves as the rotation axis, with respect to the operation portion 211. A front end portion 2121 of the hook portion 212 has a tapered shape in which the outer diameter gradually decreases toward the forward side. A branched portion 2122 that is branched into two portions is formed in a forward portion of the hook portion 212 that includes the front end portion 2121. A depressed inner slide groove 2123 that extends anteroposteriorly is formed on each inner surface of the branched portion 2122.

A depressed outer slide groove 2124 (see FIG. 8B) that extends anteroposteriorly is formed on the outer surface of the hook portion 212 in an outer area with respect to the circumference of the inner slide groove 2123. An extension end portion of the outer slide groove 2124 on the forward side communicates with a forward engagement hole 2125 (see FIG. 8B) that is formed in the hook portion 212. On the other hand, an extension end portion of the outer slide groove 2124 on the backward side communicates with a backward engagement hole 2126 (see FIG. 8B) that is formed in the hook portion 212.

The cover member 22 is cylindrical and extends anteroposteriorly. The back side of the cover member 22 is sealed with a back plate 221. An outer circumferential portion of the back plate 221 protrudes radially from the outer circumferential surface of a cover member body 222. A through hole 223 is formed at a center portion of the back side of the back plate 221. The hook portion 212 of the operation member 21 penetrates through the through hole 223.

The holding member 23 is approximately cylindrical and includes a support portion 231 and a claw portion 232. The support portion 231 has a cylindrical shape on the posterior side of the holding member 23. Notches are formed at intervals in the support portion 231. The claw portion 232 is contiguous to the support portion 231 and the notches that extend in the axial direction are formed at certain intervals in the circumferential direction, which provides a plurality of (four in the example illustrated in the drawings) claws 2321, the outer diameters of which gradually decrease toward the tip. The size of claw portion 32 in the radial direction can be arbitrarily changed, i.e., the diameter of the claw portion 32 is increasable.

The holding member 23 is inserted into the endoscope hood 10 while the claw portion 232 has a reduced diameter, and the holding member 23 holds the endoscope hood 10. More specifically, the diameter of the claw portion 232 of the holding member 23 is reduced using dedicated equipment and the holding member 23 is inserted into the endoscope hood 10 with the reduced diameter so that the holding member 23 thereby holds the endoscope hood 10. Thereafter, the dedicated equipment is detached.

A positioning member (pushing member) 26 enters the holding member 23 such that the mutual positional relationship is defined. The mutual positional relationship will be described here. When the endoscope hood 10 is attached to the endoscope tip portion 2 to which the endoscope hood 10 is to be attached, the amount in which the endoscope hood 10 deviates from the tip 3 of the endoscope 1 is defined as a predetermined amount. The positioning member 26 is cylindrical with a diameter smaller than that of the holding member 23. The positioning member 26 includes an engagement portion 261 and an abut portion 262.

The engagement portion 261 is a backward portion of the positioning member. A cutout is formed in the engagement portion 261 and thus the engagement portion 261 is forked. A protrusion 2611 that protrudes backward is formed in each extension end portion of the engagement portion 261. An engagement protrusion 2612 (see FIG. 8F) that protrudes inward is formed on the inner surface of each of the protrusions 2611.

Notches that extend in the axial direction are formed at certain intervals in the circumferential direction so that the abut portion 262 includes a plurality of (four in the example illustrated in the drawings) abut claws 2621. An inner extension portion that extends inward is formed on the front end of each of the abut claws 2621 so that positioning end portions 2622 are provided. The size of the abut portion 262 in the radial direction can be changed arbitrarily, i.e., the diameter of the abut portion 262 is increasable.

In the positioning member 26, the abut claws 2621 that are components of the abut portion 262 protrude outward from the claws 2321 that are components of the claw portion 232 of the holding member 23. The abut portion 262 is positioned behind the endoscope hood 10 that is held by the holding member 23.

The holding member 23 and the positioning member 26 enter the cover member 22 from the anterior side and the positioning member 26 penetrates through the through hole 223. The hook portion 212 of the operation member 21 enters the positioning member 26, which penetrates through the through hole 223, and the engagement protrusions 2612 of the engagement portion 261 of the positioning member 26 enter the backward engagement hole 2126 of the hook portion 212 from the outside so that the positioning member 26 engages with the operation member 21.

The diameter increasing member 24 includes a pin portion 241 and a widening portion 242. The pin portion 241 is elongated. A lock protrusion 2411 (see FIG. 8F) that protrudes outward is formed on each side surface of the extension end portion, i.e., backward end portion. The widening portion 242 is contiguous to the pin portion 241. The maximum width of the widening portion 242 gradually increases to the forward side.

In the diameter increasing member 24, the pin portion 241 enters the holding member 23 and the positioning member 26 and further enters the hook portion 212 of the operation member 21 from the forward side, and the lock protrusions 2411 enter the inner slide grooves 2123 of the hook portion 212. Accordingly, the diameter increasing member 24 is locked together with the operation member 21. In addition, the widening portion 242 of the diameter increasing member 24 is positioned ahead of the endoscope hood 10, which is held by the holding member 23, such that the endoscope hood 10 is not detached from the holding member 23.

The external cylindrical member 25 is cylindrical and has an outer diameter slightly smaller than the inner diameter of the cover member 22. Most of the circumferential wall portion of the external cylindrical member 25 is removed except for a part on the backward end side (hereinafter "a backward end portion 251"). The external cylindrical member 25 enters the cover member 22 from the anterior side such that the holding member 23, the positioning member 26, and the diameter increasing member 24 relatively enters the external cylindrical member 25, and a protrusion 224 of the cover member 22 enters a hole (not shown) that is formed in the backward end portion 251. Accordingly, the external cylindrical member 25 engages with the cover member 22.

A guide member 252 is formed on the front end surface of the external cylindrical member 25. The guide member 252 is ring-shaped and is formed from an elastic material, such as a sponge. A guide hole 2521 is formed at a center portion of the guide member. The guide hole 2521 has a diameter slightly smaller than the outer diameter of the endoscope tip portion 2.

In the above-described hood attachment jig 20, the positions of the members are adjusted such that the center axes of the operation member 21 (the hook portion 212), the cover member 22, the holding member 23, the positioning member 26, the diameter increasing member 24, and the external cylindrical member 25 are positioned on the same straight line.

The endoscope hood 10, which is held by the holding member 23, can be attached to the endoscope tip portion 2 by using the hood attachment jig 20 that has the above-described configuration.

FIGS. 7 to 16 illustrate the procedure of attachment of the endoscope hood 10 using the hood attachment jig 20 according to the embodiment of the present invention. With reference to these drawings, attaching the endoscope hood 10 using the hood attachment jig 20 will be explained below.

Figure 7:
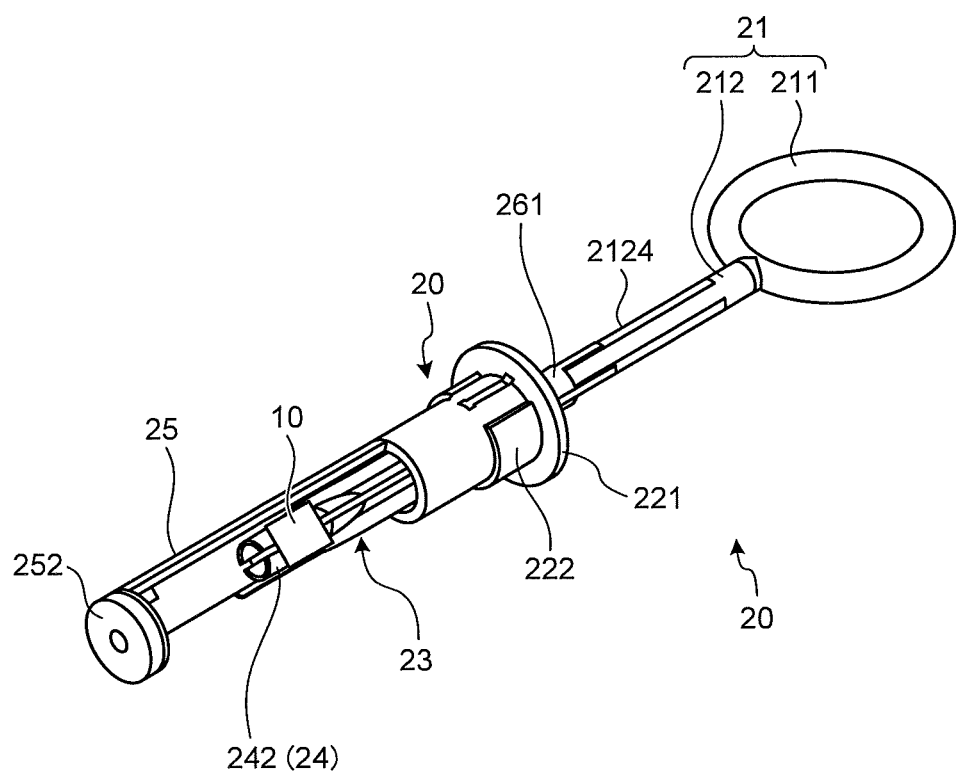
FIG. 7 is a perspective view illustrating a case where a diameter increasing operation is performed using an operation member that is a component of the hood attachment jig illustrated in FIG. 5.
Figure 8A:
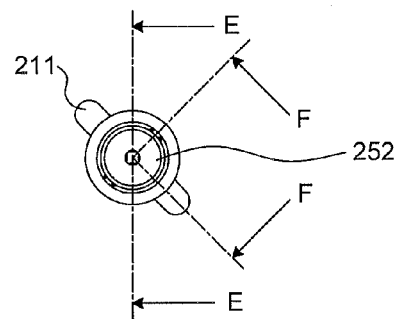
FIG. 8A is a front view of the hood attachment jig illustrating the diameter increasing operation, which is performed using the operation member illustrated in FIG. 5.
Figure 8B:
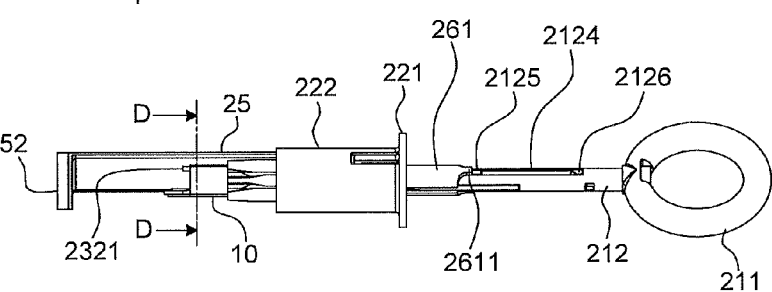
FIG. 8B is a side view of FIG. 8A.
Figure 8C:
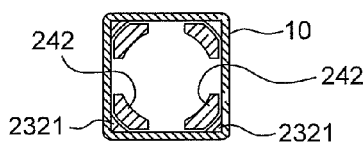
FIG. 8C is a cross-sectional view along the line D-D in FIG. 8B.
Figure 8D:
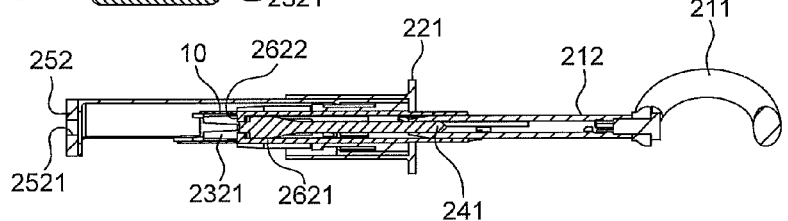
FIG. 8D is a cross-sectional view along the line E-E in FIG. 8A.
Figure 8E:
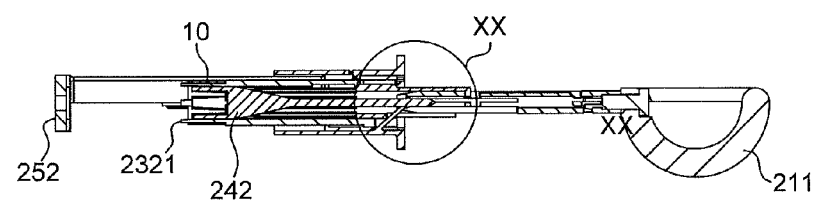
FIG. 8E is a cross-sectional view along the line F-F in FIG. 8A.
Figure 8F:
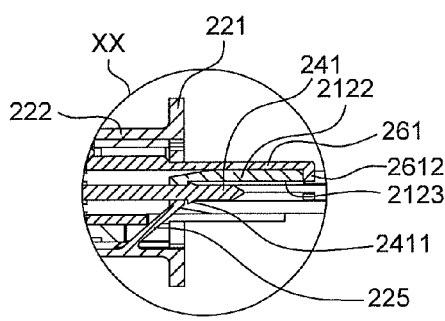
FIG. 8F is a enlarged partial view of FIG. 8E.
Figure 9A:
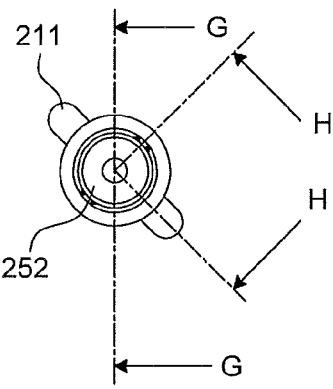
FIG. 9A is a front view illustrating a state where the endoscope, to which the endoscope hood is to be attached, is approaching the hood attachment jig illustrated in FIG. 5.
Figure 9B:
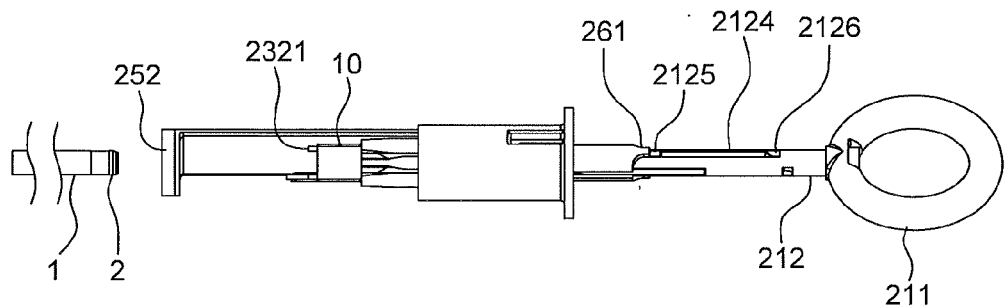
FIG. 9B is a side view of FIG. 9A.
Figure 9C:
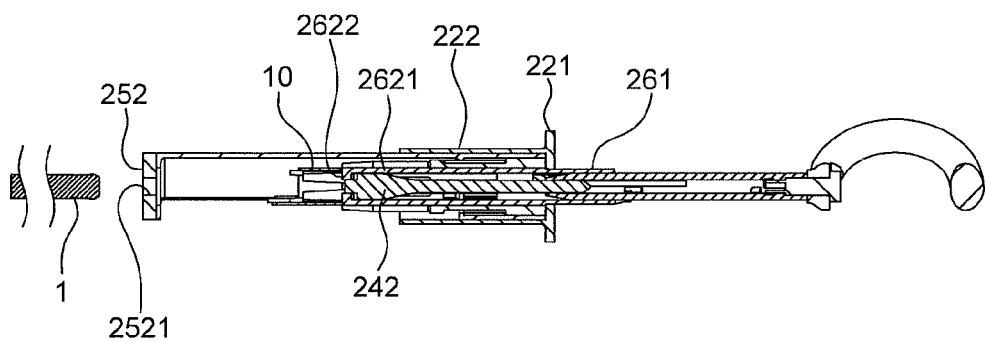
FIG. 9C is a cross-sectional view along the line G-G in FIG. 9A.
Figure 9D:
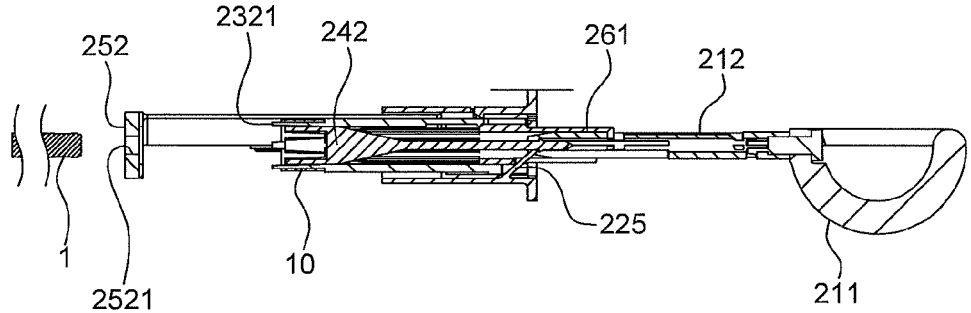
FIG. 9D is a cross-sectional view along the line H-H in FIG. 9A.
Figure 10A:
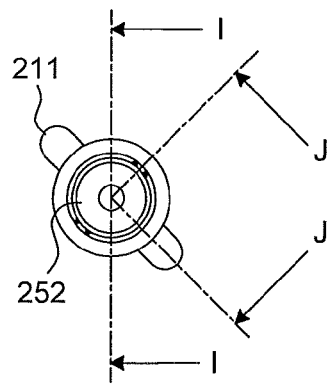
FIG. 10A is a front view illustrating a state where the endoscope, to which the endoscope hood is to be attached, is approaching the hood attachment jig illustrated in FIG. 5.
Figure 10B:
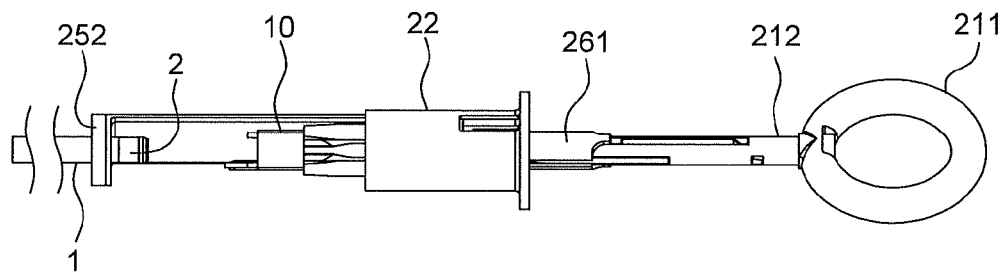
FIG. 10B is a side view of FIG. 10A.
Figure 10C:
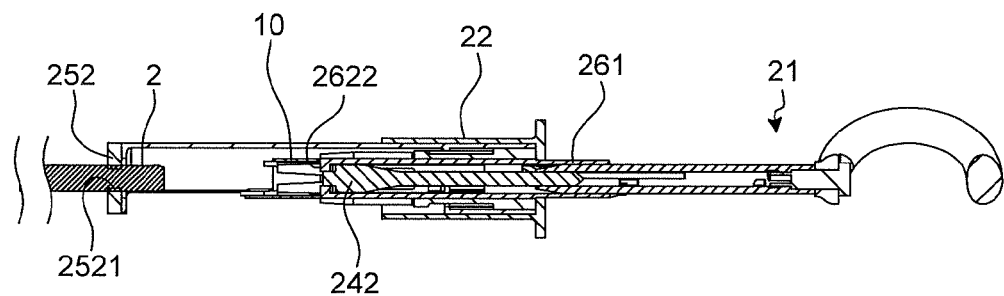
FIG. 10C is a cross-sectional view along the line I-I in FIG. 10A.
Figure 10D:
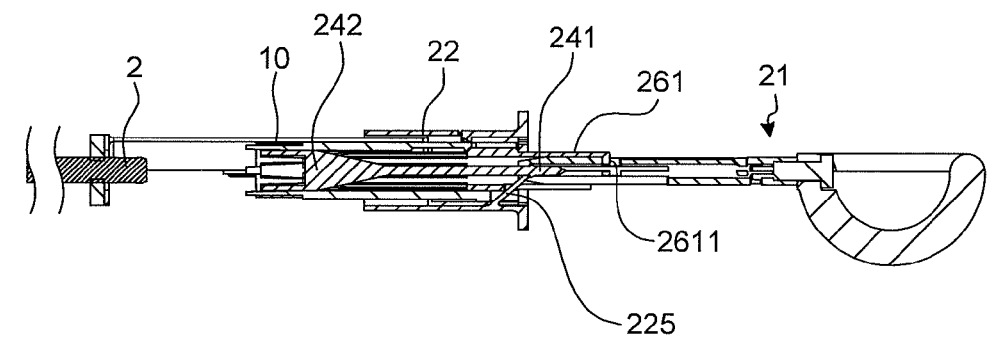
FIG. 10D is a cross-sectional view along the line J-J in FIG. 10A.
Figure 11A:
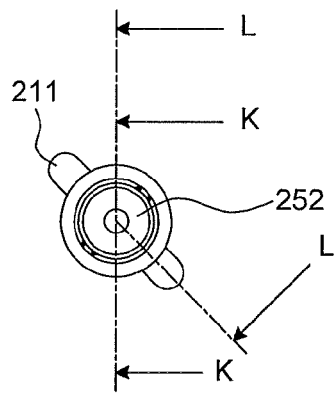
FIG. 11A is a front view illustrating a state where the endoscope enters a holding member with an increased diameter.
Figure 11B:
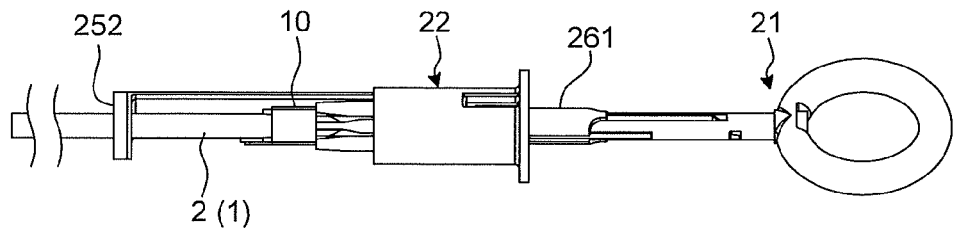
FIG. 11B is a side view of FIG. 11A.
Figure 11C:
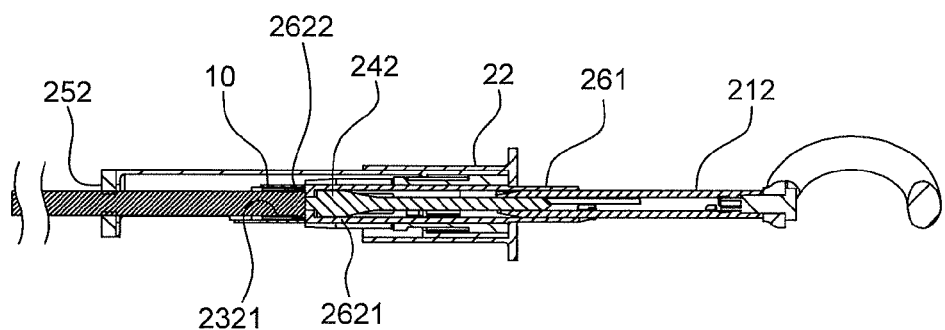
FIG. 11C is a cross-sectional view along the line K-K in FIG. 11A.
Figure 11D:
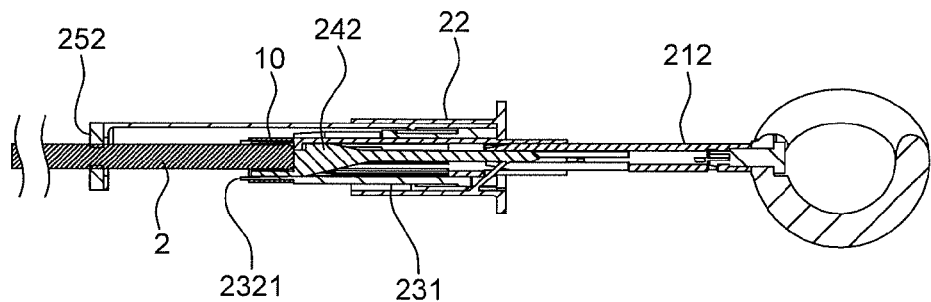
FIG. 11D is a cross-sectional view along the line L-L in FIG. 11A.
Figure 12A:
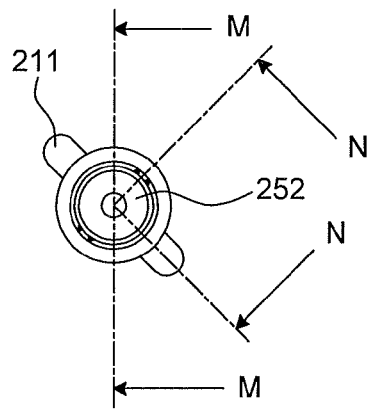
FIG. 12A is a front view illustrating a state where the endoscope enters the holding member with the increased diameter.
Figure 12B:
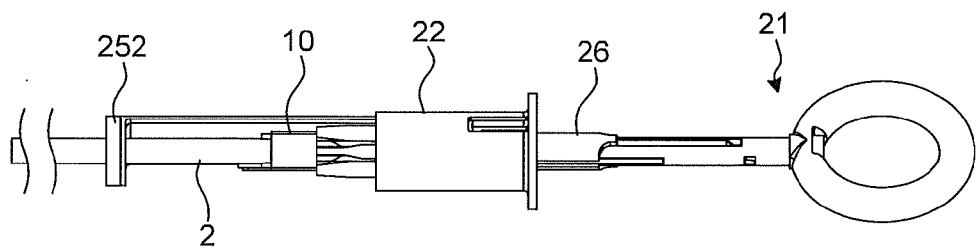
FIG. 12B is a side view of FIG. 12A.
Figure 12C:
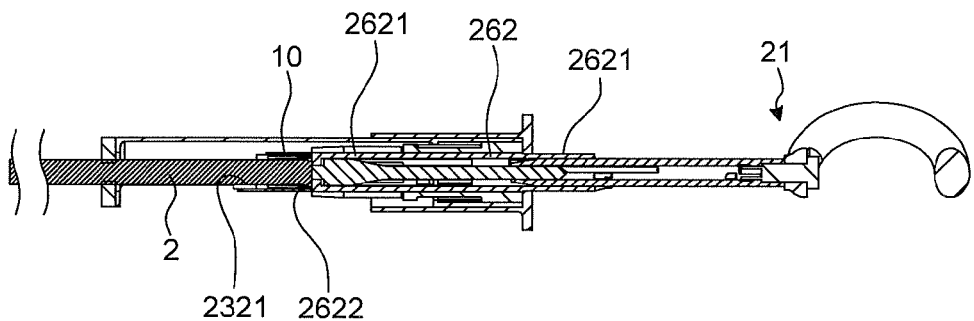
FIG. 12C is a cross-sectional view along the line M-M in FIG. 12A.
Figure 12D:
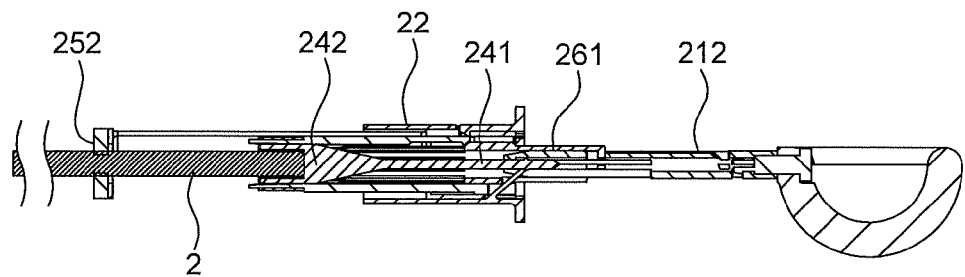
FIG. 12D is a cross-sectional view along the line N-N in FIG. 12A.
Figure 13A:
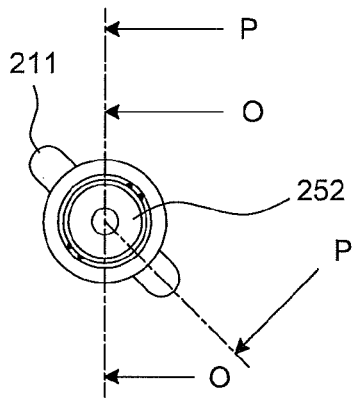
FIG. 13A is a front view illustrating the hood attachment jig illustrating a case where the attachment operation is performed using the operation member.
Figure 13B:
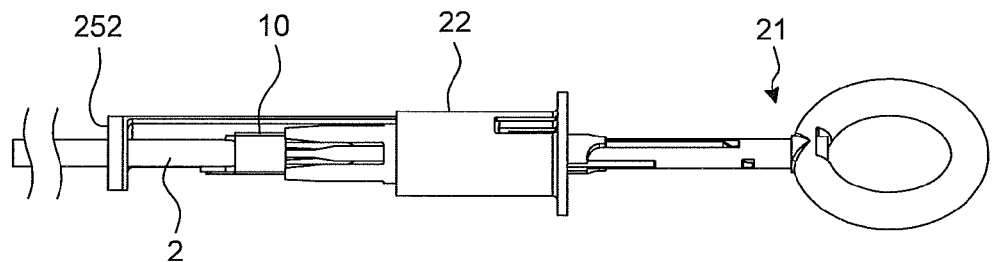
FIG. 13B is a side view of FIG. 13A.
Figure 13C:
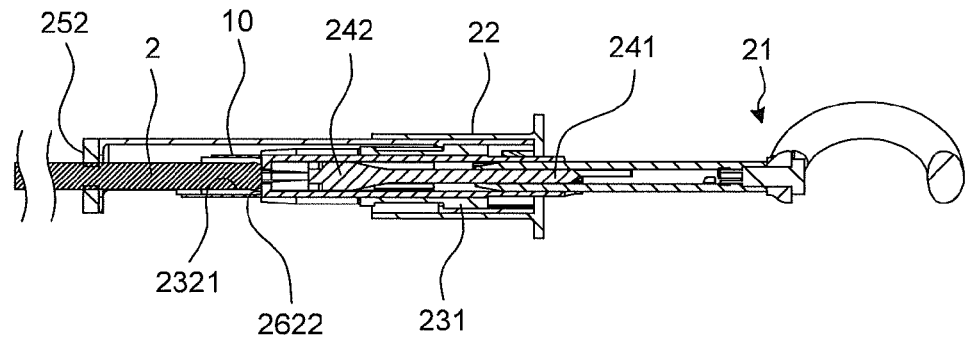
FIG. 13C is a cross-sectional view along the line O-O in FIG. 13A.
Figure 13D:
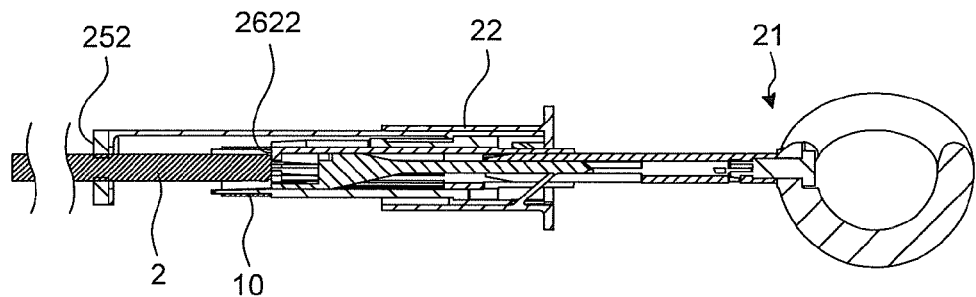
FIG. 13D is a cross-sectional view along the line P-P in FIG. 13A.
Figure 14A:
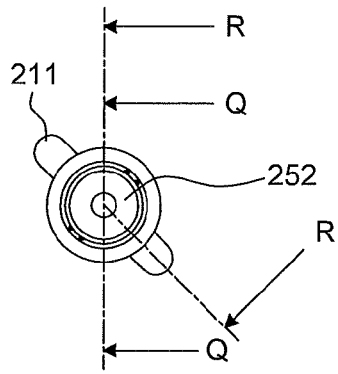
FIG. 14A is a front view illustrating a state where a positioning member pushes out the holding member and the endoscope.
Figure 14B:
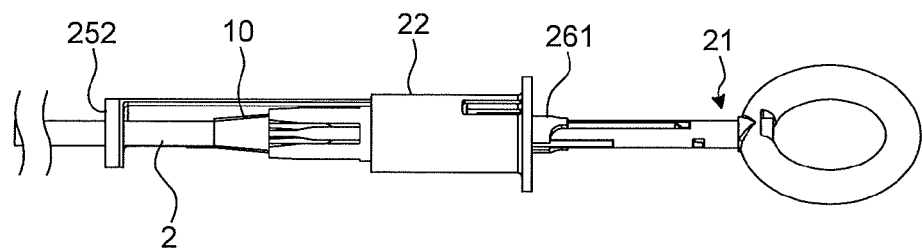
FIG. 14B is a side view of FIG. 14A.
Figure 14C:
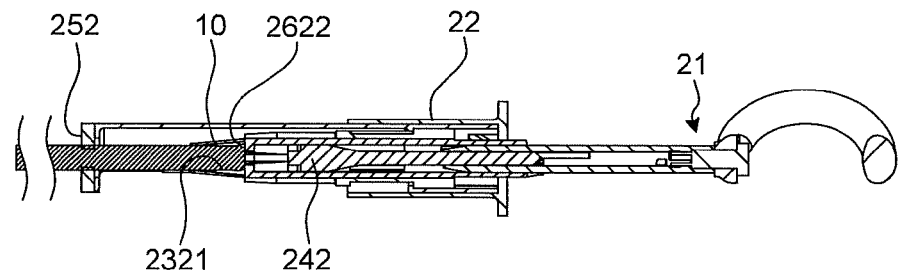
FIG. 14C is a cross-sectional view along the line Q-Q in FIG. 14C.
Figure 14D:
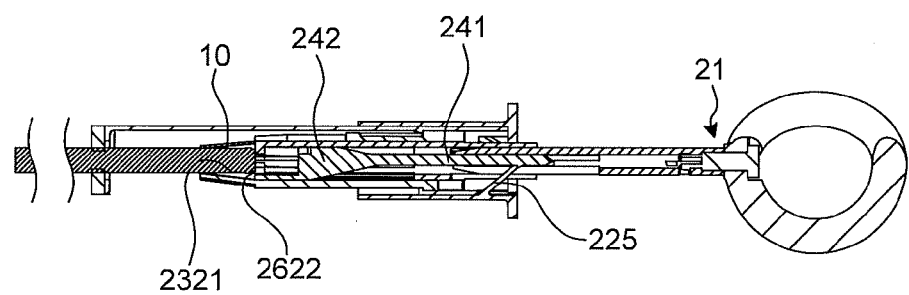
FIG. 14D is a cross-sectional view along the line R-R in FIG. 14A.
Figure 15A:
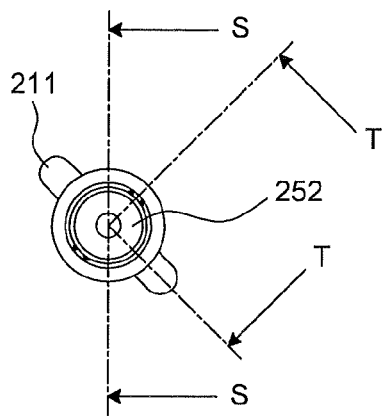
FIG. 15A is a front view illustrating a state where the positioning member pushes out the endoscope.
Figure 15B:
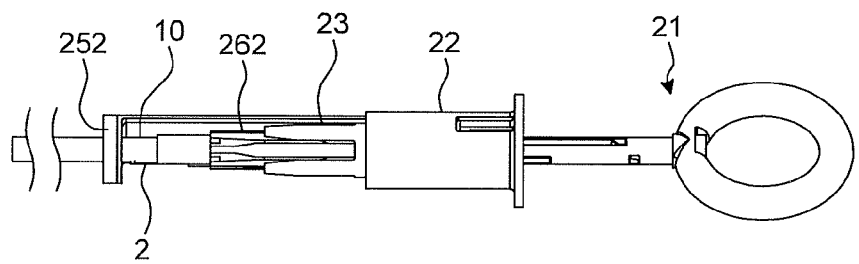
FIG. 15B is a side view of FIG. 15A.
Figure 15C:
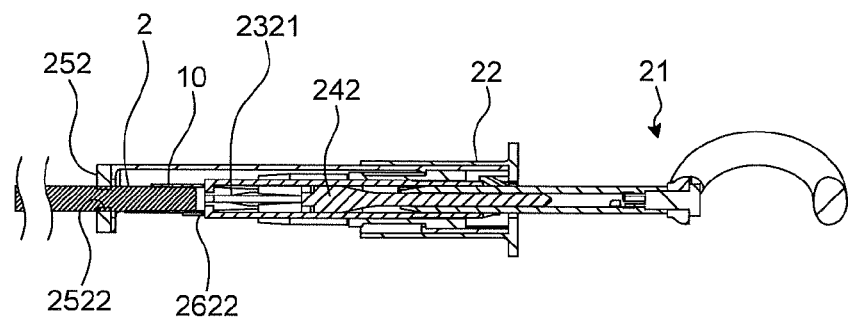
FIG. 15C is a cross-sectional view along the line S-S in FIG. 15A.
Figure 15D:
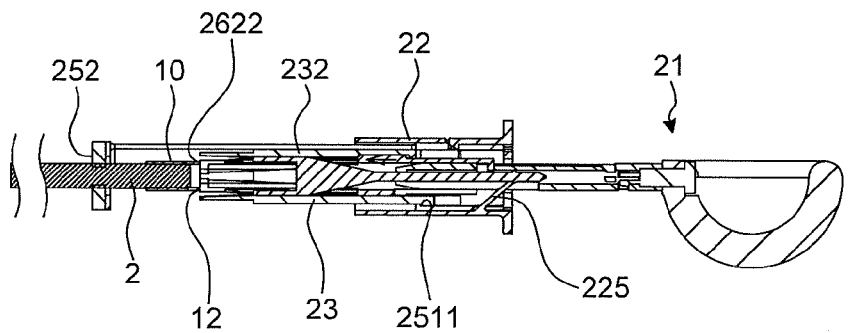
FIG. 15D is a cross-sectional view along the line T-T in FIG. 15A.
Figure 16A:
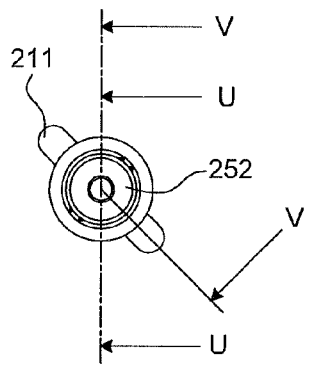
FIG. 16A is a front view illustrating a state where the hood attachment jig is separated from the endoscope to which the endoscope hood is attached.
Figure 16B:
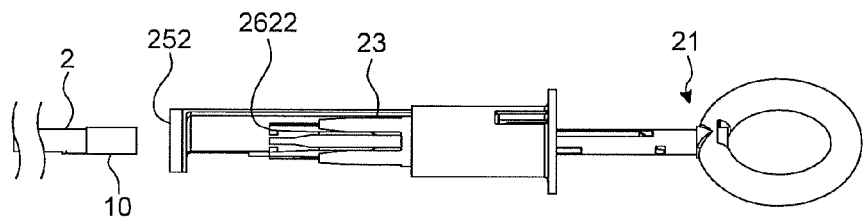
FIG. 16B is a side view of FIG. 16A.
Figure 16C:
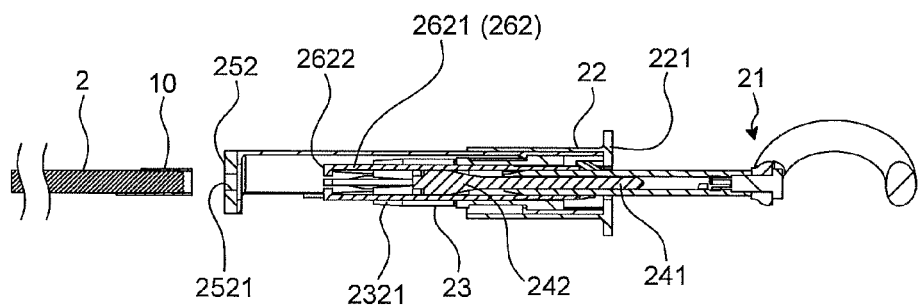
FIG. 16C is a cross-sectional view along the line U-U in FIG. 16A.
Figure 16D:
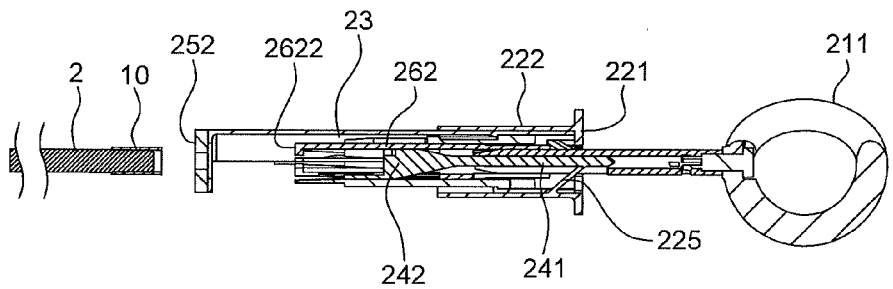
FIG. 16D is a cross-sectional view along the line V-V in FIG. 16A.

As illustrated in FIG. 7 and FIGS. 8A to 8F, when the operation portion 211 of the operation member 21 is gripped to perform an operation for shifting the operation member 21 to the posterior side, i.e., a diameter increasing operation is performed, the diameter increasing member 24 that is locked together with the hook portion 212 of the operation member 21 slides back with the operation member 21. FIG. 7 and FIGS. 8A to 8F illustrate a case where the diameter increasing operation is performed using the operation member 21 that is a component of the hood attachment jig 20. FIG. 7 is a perspective view of the hood attachment jig 20, FIG. 8A is a front view of the hood attachment jig 20, FIG. 8B is a side view of FIG. 8A, FIG. 8C is a cross-sectional view along the line D-D in FIG. 8B, FIG. 8D is a cross-sectional view along the line E-E in FIG. 8A, FIG. 8E is a cross-sectional view along the line F-F in FIG. 8A, and FIG. 8F is an enlarged partial view of FIG. 8E.

In this case, in the positioning member 26 that engages with the hook portion 212, the engagement protrusions 2612 are detached from the backward engagement hole 2126, slide on the outer slide groove 2124, and then enter the forward engagement hole 2125. In other words, the positioning member 26 and the holding member 23, having the defined positional relationship with the positioning member 26, do not slide and thus keep their original positions.

Accordingly, the diameter increasing member 24 that slides back with the operation member 21 enters the holding member 23 (the positioning member 26) from the forward side and then the widening portion 242 of the diameter increasing member 24 enters the holding member 23 so that the diameter of the holding member 23 increases. This increases the diameter of the endoscope hood 10 (particularly, see FIG. 8C). The diameter increasing member 24 (the widening portion 242) is not brought into contact with the endoscope hood 10.

In addition, as illustrated in FIG. 8F, the pin portion 241 of the diameter increasing member 24, which slides back, abuts on a locking slip 225 that is provided on the cover member 22. Accordingly, the forward movement of the diameter increasing member 24 is regulated.

Thereafter, the endoscope tip portion 2 to which the hood attachment jig 20 is to be attached approaches from the anterior side of the hood attachment jig 20, as illustrated in FIGS. 9A to 9D, and then passes through the guide hole 2521, as illustrated in FIGS. 10A to 10D. As described above, the inner diameter of the guide hole 2521 is slightly smaller than the outer diameter of the endoscope tip portion 2. Furthermore, the guide member 252 in which the guide hole 2521 is formed is made of an elastic member, such as a sponge.

Accordingly, when the endoscope tip portion 2 is passing through the guide hole 2521, the diameter of the guide hole 2521 increases by the elastic deformation of the guide member 252 and thus the periphery of the guide hole 2521 slides while making contact with the outer circumferential surface of the endoscope tip portion 2.

As illustrated in FIGS. 11A to 11D, the endoscope tip portion 2, which has passed through the guide hole 2521, enters, from the front side, the holding member 23 whose diameter is increased by the diameter increasing member 24, and the tip 3 of the endoscope 1 abuts on the positioning end portions 2622 on the front ends of the abut claws 2621 of the positioning member 26. This regulates the entering of the endoscope 1 (see FIGS. 11C and 11D). The guide hole 2521 has a function for guiding the endoscope 1 into the holding member 23.

As illustrated in FIGS. 12A to 12D and FIGS. 13A to 13D, when the operation portion 211 of the operation member 21 is gripped and an operation for shifting the operation member 21 forward, i.e., when an attachment operation is performed in the state where the endoscope tip portion 2 enters the holding member 23 with increased diameter, the positioning member 26 that engages with the hook portion 212 of the operation member 21 slides forward. In this case, the positioning member 26 pushes out the holding member 23, having the defined positional relationship with the positioning member 26, and the endoscope 1 that abuts on the positioning end portion 2622, and the positioning member 26 slides them forward. In other words, when the attachment operation is performed using the operation member 21, the positioning member 26, the holding member 23 (the endoscope hood 10), and the endoscope 1 simultaneously slide forward (see particularly FIGS. 12C and 12D and FIGS. 13C and 13D).

As described above, in the diameter increasing member 24, the lock protrusion 2411 of the pin portion 241 abuts on the locking slip 225 of the cover member 22 so that forward movement of the diameter increasing member 24 is regulated. Accordingly, the lock protrusion 2411 slides on the inner slide groove 2123 of the pin portion 241.

Once the attachment operation is performed using the operation member 21 and thus the positioning member 26 that engages with the operation member 21 pushes out the holding member 23 (including the endoscope hood 10) and the endoscope 1 to slide them forward, the claw portion 232 of the holding member 23 moves forward with respect to the widening portion 242 of the diameter increasing member 24, as illustrated in FIG. 14. Accordingly, the state in which the diameter of the claw portion 232 is increased by the widening portion 242 is freed. Thus, the diameter of the claw portion 232 decreases because of the force of restitution of the endoscope hood 10 that the claw portion 232 holds.

The holding member 23 with the reduced diameter is brought into contact with the endoscope tip portion 2. A part of the endoscope hood 10 (specifically, the grip 13 or the fixation portion 11) that the holding member 23 holds is brought into contact with the outer circumferential surface of the endoscope tip portion 2 because of the force of restitution of the endoscope hood 10.

As illustrated in FIGS. 15A to 15D, a part of the holding member 23 that is pushed out by the positioning member and thus slides forward with the endoscope 1 abuts on a regulation piece 2511 that is formed on the inner surface of the backward end portion 251 of the external cylindrical member 25, which regulates further forward movement of the holding member 23. In other words, the regulation piece 2511 is a regulation member that regulates the amount of movement of the holding member 23 that is pushed.

Accordingly, the positioning member 26 that engages with the operation member 21 pushes out the endoscope 1 and thus the endoscope hood 10 that is held by the holding member 23 is pressed against the endoscope tip portion 2 from the base end side because of the force of restitution of the endoscope hood 10. Thereafter, as illustrated in FIG. 3, the endoscope hood 10 is attached to the tip portion 2 such that the endoscope hood 10 covers the outer circumferential surface of the endoscope tip portion 2 and the positioning member 26 pushes out the endoscope tip portion 2 to which the endoscope hood 10 is attached (see particularly FIGS. 15C and 15D).

As described above, the positioning member 26 serves as a push-out member. When the attachment operation is performed in the state where the endoscope tip portion 2 enters the holding member 23 whose diameter is increased, the positioning member 26 pushes out the holding member 23 and the endoscope 1 to separate them from the diameter increasing member 24. Thus, the endoscope hood 10, the force of restitution of which reduces the diameter of the holding member 23, is brought into contact with the outer circumferential surface of the endoscope tip portion 2. The positioning member 26 further pushes out the endoscope 1 to detach the endoscope 1 from the holding member 23 so that the endoscope hood 10 is attached to the endoscope tip portion 2.

As illustrated in FIGS. 16A to 16D, the hood attachment jig 20 is separated from the endoscope 1 with the tip portion 2 to which the endoscope hood 10 is attached, so that attachment of the endoscope hood 10 is completed.

As described above, in the hood attachment jig 20 according to the embodiment, the holding member 23 whose diameter is increasable holds the endoscope hood 10 in the state where the holding member 23 is inserted into the endoscope hood 10. When the diameter increasing operation is performed, the diameter increasing member 24 enters the holding member 23, thereby increasing the diameter of the endoscope hood 10. When the attachment operation is performed in the state where the endoscope tip portion 2 enters the holding member 23 with the increased diameter, the positioning member 26 pushes out the holding member 23 and the endoscope 1 to separate them from the diameter increasing member 24. Accordingly, the endoscope hood 10, the force of restitution of which reduces the diameter of the holding member 23, is brought into contact with the outer circumferential surface of the endoscope tip portion 2. Furthermore, the positioning member 26 pushes out the endoscope 1 to detach the endoscope 1 from the holding member 23 so that the endoscope tip portion 2 is attached to the endoscope hood 10. Accordingly, the endoscope hood 10 can be maintained as it is in a normal state. Furthermore, when the endoscope hood 10 is attached, the diameter of the endoscope hood 10 is increased and the endoscope tip portion 2 is then relatively inserted into the endoscope hood 10. Thereafter, the force of restitution of the endoscope hood 10 reduces the diameter of the endoscope hood 10 and thus the endoscope hood 10 can be attached to the endoscope tip portion 2. Accordingly, the endoscope hood 10 can be maintained as it is in a normal state and the endoscope hood 10 can be preferably attached to the endoscope tip portion 2, which has a sufficiently small diameter.

In the hood attachment jig 20, the endoscope hood 10 is maintained as it is in a normal state and the diameter of the endoscope hood 10 is only increased when the endoscope hood 10 is being attached. Thus, there is no risk that the endoscope hood 10 deforms during storage and accordingly the endoscope hood 10 can be stored for a long period.

In addition, in the hood attachment jig 20, the positioning member 26 abuts on the endoscope tip portion 2 that enters the holding member 23 with the increased diameter and the positioning member 26 includes the positioning end portion 2622 that defines the amount of protrusion of the endoscope hood 10 from the endoscope tip portion 2 when the endoscope hood 10, which is held by the holding member 23, is attached to the endoscope tip portion 2. This makes it possible to preferably attach the endoscope hood 10 to the endoscope tip portion 2 with sufficiently high accuracy.

Furthermore, in the hood attachment jig 20, the guide member 252 with which the external cylindrical member 25 is provided has a role for guiding the endoscope 1, which passes through the guide hole 2521, into the holding member 23, whose diameter is increased. The guide hole 2521 has a diameter slightly smaller than the outer diameter of the endoscope tip portion 2. The diameter of the guide hole 2521 increases because of the elastic deformation when the endoscope 1 is passing through the guide hole 2521 and slides and makes contact with the outer circumferential surface of the endoscope 1 so that the body fluid or a lubricant that is applied on the outer circumferential surface of the endoscope tip portion 2 can be rubbed off. Accordingly, the endoscope hood 10 can be preferably attached to the endoscope tip portion 2.

The preferred embodiment of the present invention is explained above. However, the present invention is not limited to this and various modifications can be made.

In the above-described embodiment, the extension end portion 151 of the cutout 15 is positioned between the end 141 of the groove portion 14 and the same groove portion 14 adjacent to the end 141. Alternatively, in the present invention, the cutout 15 may be positioned between the adjacent groove portions 14. This also allows the tearing from the cutout 15 to reach any one site on the groove portion 14 and the endoscope hood 10 to be torn in the direction in which the groove portion 14 extends and for the fixation portion 11 to fracture. The expression "between the adjacent groove portions 14" refers to between the adjacent grooves in a predetermined area on the outer surface of the endoscope hood 10.

In the embodiment, the groove portion 14 is explained as one that is formed spirally. However, it is satisfactory if the groove is generally formed spirally, i.e., the groove may be partly formed linearly. Particularly when the endoscope hood 10 is formed by attaching parts, it is preferable that the groove portion 14 in a parting portion be formed approximately linearly in consideration of convenience when manufacturing a mold or molding.

The hood attachment jig according to the present invention may be provided with a determining mechanism for determining the state in which the endoscope hood is attached to the endoscope tip portion. In the hood attachment jig according to the present invention, when the attachment operation is performed, the push-out member (the positioning member) may perform pushing-out by the reaction force of an incorporated spring. Using the reaction force of a spring allows forward sliding of the positioning member at a certain speed. Accordingly, the endoscope hood can be attached preferably.

Note 1:

An endoscope hood in which a cylindrical fixation portion is fixed by pressure such that the fixation portion covers an outer circumferential surface of a tip portion of an endoscope so that the endoscope hood is attached to a tip portion of the endoscope in a state where a protrusion portion that is contiguous to a tip of the fixation portion protrudes from a tip of the endoscope and where a grip that is contiguous to a base end of the fixation portion makes contact with an outer circumferential surface of the endoscope, the endoscope hood including:

a groove portion that is formed spirally on an outer surface of the fixation portion such that an end of the groove portion extends over an outer surface of the grip; and a cutout that is formed at a boundary between the fixation portion and the grip and extends between adjacent groove portions.

Note 2:

The endoscope hood according to note 1, wherein the cutout extends between the end of the groove portion and the same groove portion that is adjacent to the end.

Note 3:

The endoscope hood according to note 1 or 2, wherein the grip is formed to have a thickness smaller than at least that of the fixation portion.

Note 4:

The endoscope hood according to any one of notes 1 to 3, wherein the endoscope hood is formed of a material that contains an added contrast agent.

In the above-described embodiment, the holding member whose diameter is increasable holds the endoscope hood in a state where the holding member whose diameter is increasable is inserted into the endoscope hood. When a diameter increasing operation is performed, the diameter increasing member increases the diameter of the holding member by entering the holding member so that the diameter of the endoscope hood increases. When an attachment operation is performed in a state where the tip portion of the endoscope enters the holding member with the increased diameter, the push-out member pushes out the holding member and the endoscope to separate the holding member and the endoscope from the diameter increasing member. Thus, the endoscope hood, whose force of restitution reduces the diameter of the holding member, is brought into contact with the outer circumferential surface of the endoscope tip portion. The positioning member further pushes out the endoscope to separate the endoscope from the holding member so that the endoscope hood is attached to the endoscope tip portion. Accordingly, the endoscope hood can be maintained as it is in a normal state. Furthermore, when the endoscope hood is attached, the diameter of the endoscope hood is increased and the endoscope tip portion is then relatively inserted into the endoscope hood. Thereafter, the force of restitution of the endoscope hood reduces the diameter of the endoscope hood and thus the endoscope hood can be attached to the endoscope tip portion. Accordingly, the endoscope hood can be maintained as it is in a normal state and the endoscope hood can be preferably attached to an endoscope tip portion that has a sufficiently small diameter.

The above and other features, advantages and technical and industrial significance of this invention will be better understood by reading the following detailed description of presently preferred embodiments of the invention, when considered in connection with the accompanying drawings.

What is claimed is:

1. A hood attachment jig for attaching an approximately cylindrical endoscope hood to an endoscope such that the endoscope hood covers an outer circumferential surface of a tip portion of the endoscope, the hood attachment jig comprising:
    a holding member whose diameter is increasable and that holds the endoscope hood in a state where the holding member is inserted into the endoscope hood;
    a diameter increasing member that increases the diameter of the holding member by entering the holding member from a forward side of the holding member, so that the diameter of the endoscope hood increases; and
    a push-out member that, when an attachment operation is performed in a state where the tip portion of the endoscope enters the holding member with the increased diameter, pushes out the holding member and the endoscope to separate the holding member and the endoscope from the diameter increasing member so that the endoscope hood, a force of restitution of which reduces the diameter of the holding member, is brought into contact with the outer circumferential surface of the tip portion of the endoscope and further pushes out the endoscope to detach the endoscope from the holding member so that the endoscope hood is attached to the endoscope tip portion.

2. The hood attachment jig according to claim 1, wherein the push-out member includes a positioning end portion that is brought into contact with the tip portion of the endoscope that enters the holding member with the increased diameter and that defines an amount in which the endoscope hood, which is held by the holding member, protrudes from the tip portion of the endoscope when the endoscope hood is attached to the tip portion.

3. The hood attachment jig according to claim 1, further comprising a regulation member that regulates an amount of movement of the holding member that is pushed out by the push-out member.

4. The hood attachment jig according to claim 1, further comprising a guide member that allows the endoscope to pass through a hole that is formed in the guide member and guides the tip portion of the endoscope into the holding member with the increased diameter.

5. The hood attachment jig according to claim 4, wherein the guide member is formed from an elastic material and a diameter of the hole is smaller than that of the tip portion of the endoscope.

6. The hood attachment jig according to claim 1, wherein:
    the center axes of the holding member, the diameter increasing member and the push-out member are arranged on an anteroposterior axis of the hood attachment jig;
    the diameter increasing member is configured to enter the holding member from an anterior side of the holding member;
    the tip portion of the endoscope enters the holding member from the anterior side of the holding member; and
    the push-out member is configured to push out the holding member and the endoscope, with respect to the diameter increasing member, toward an anterior side of the anteroposterior axis and to further push out the tip portion of the endoscope, with respect to the holding member, toward the anterior side of the anteroposterior axis.

7. The hood attachment jig according to claim 6, wherein:
    the holding member comprises a claw portion having a diameter that is increasable by the diameter increasing member; and
    the claw portion is inserted into the endoscope hood while the claw portion has a reduced diameter so that the claw portion thereby holds the endoscope hood.

8. The hood attachment jig according to claim 6, wherein the diameter increasing member comprises a widening portion having a radial width that increases towards an anterior side of the diameter increasing member.

9. The hood attachment jig according to claim 6, further comprising a diameter increasing member movement regulation member configured to regulate an amount of movement of the diameter increasing member when the push-out member pushes out the holding member and the tip portion of the endoscope, with respect to the diameter increasing member, to separate the holding member and the tip portion of the endoscope from the diameter increasing member.

* * * * *